United States Patent [19]

Berthier

[11] Patent Number: 5,429,612
[45] Date of Patent: Jul. 4, 1995

[54] SYRINGE WITH A SLIDABLE NEEDLE PROTECTION DEVICE

[75] Inventor: Michel Berthier, Vimy, France
[73] Assignee: Dentoptic, Hondainville, France
[21] Appl. No.: 64,176
[22] PCT Filed: Nov. 25, 1991
[86] PCT No.: PCT/FR91/00934
  § 371 Date: May 25, 1993
  § 102(e) Date: May 25, 1993
[87] PCT Pub. No.: WO92/09319
  PCT Pub. Date: Jun. 11, 1992

[30] Foreign Application Priority Data

Nov. 26, 1990 [FR] France ............... 90 14767

[51] Int. Cl.⁶ .................................. A61M 5/32
[52] U.S. Cl. ....................... 604/198; 604/110; 604/263
[58] Field of Search ............. 604/110, 192, 198, 263

[56] References Cited

U.S. PATENT DOCUMENTS

| 4,894,055 | 1/1990 | Sudnak . | |
|---|---|---|---|
| 4,911,693 | 3/1990 | Paris . | |
| 4,917,673 | 4/1990 | Coplin | 604/198 |
| 4,932,940 | 6/1990 | Walket et al. . | |
| 4,946,446 | 8/1990 | Vadher | 604/198 |
| 5,011,479 | 4/1991 | Le et al. | 604/198 |

FOREIGN PATENT DOCUMENTS 0250104 12/1987 European Pat. Off. .
0276160  7/1988 European Pat. Off. .
9013325 11/1990 WIPO .

Primary Examiner—Corrine Maglione
Attorney, Agent, or Firm—Griffin, Butler, Whisenhunt & Kurtossy

[57] ABSTRACT

This device for an injection syringe including a cylindrical body (2) closed at one of its ends by a transverse wall in which the needle (6) is implanted, is such that the end of the cylindrical body is fitted with a slideway (7) for a needle protector (8) that includes a first tubular portion (9) of large diameter suitable for sliding along the slideway (7) between two positions that are axially separate from each other, and a small diameter portion (10) that extends the large diameter portion longitudinally, forming a moving protective sheath for the end of the needle (6), guiding and indexing elements (11, 12, 14, 16, 22, 26) being provided in inaccessible manner between the slideway (7) and the large diameter portion (9) of the protector so as to allow the needle to be uncovered and then recovered in succession once only.

6 Claims, 1 Drawing Sheet

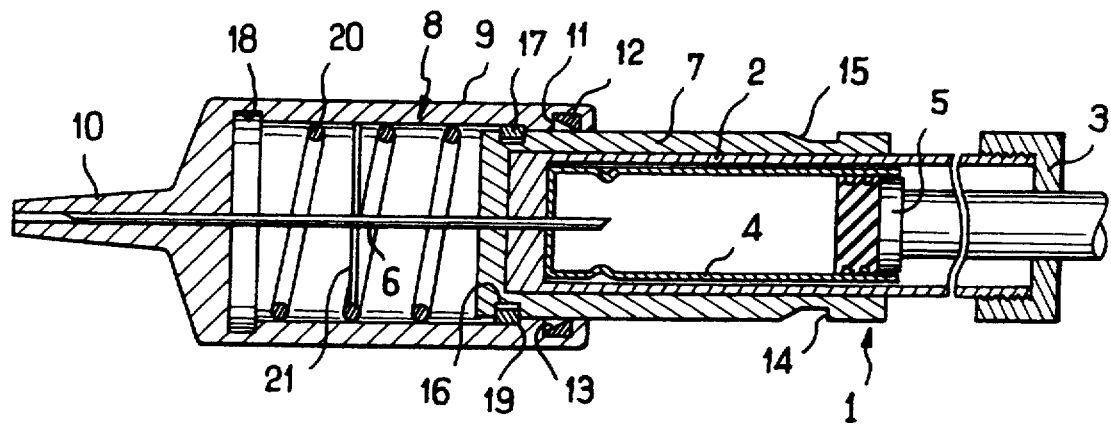
FIG_1
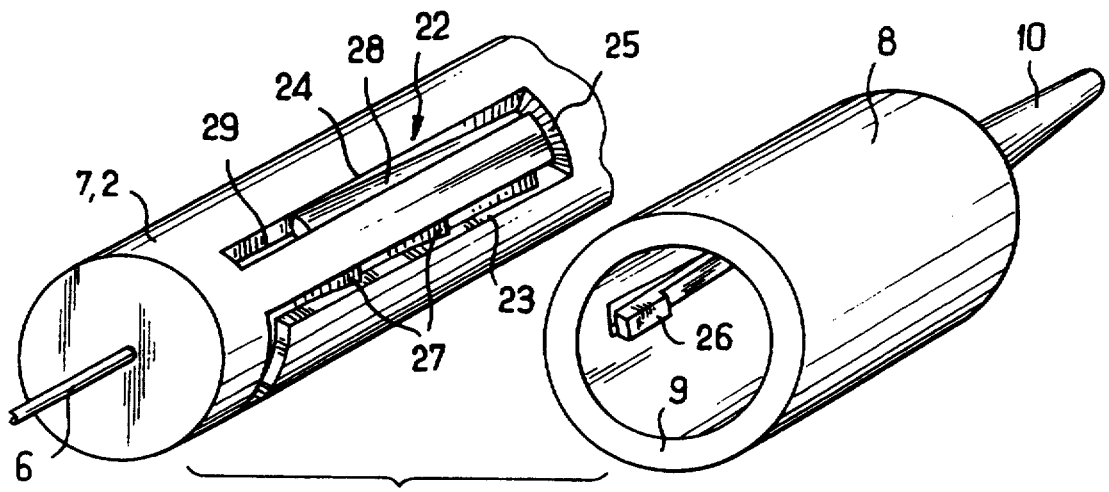
FIG_2
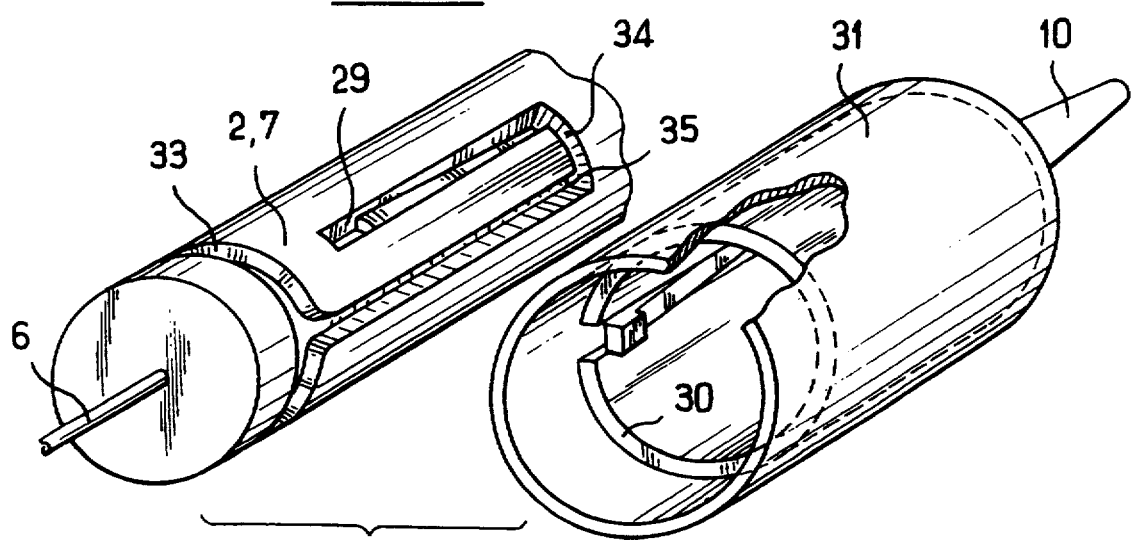
FIG_3

SYRINGE WITH A SLIDABLE NEEDLE PROTECTION DEVICE

The present invention relates to a protection device for the needle of an injection syringe.

BACKGROUND OF THE INVENTION

At present, syringes are delivered with a protector enabling them to be conserved under sterile conditions prior to use, and also enabling them to be covered after use so as to protect anyone handling the used syringe from any contamination that could result from unintentional pricks.

These dispositions are not capable of eliminating all danger of contamination after use since the user needs to put the cap back on the needle, and it is during this operation that the risk of pricking oneself is high. Furthermore, syringes re-capped in this way can still be reused, and that is very much to be avoided. That is why, in some cases, the needle in a protector is fixed to the syringe and, after use, is removed from the syringe and is broken so as to prevent reuse. Nevertheless, there remains a risk of the user being pricked during this final manipulation.

It is also recalled that certain present-day syringes include a cylindrical case having one end closed either by a partition in which the injection needle is implanted, or else by an endpiece that carries an add-on needle, and is open at its opposite end so as to receive a flask of substance to be injected, with the perforatable wall thereof being directed towards the portion of the needle that projects into the case, the case then being closed again by a plug which includes a piston for acting on a moving wall of the flask opposite from its perforatable wall.

The invention provides an improvement both over conventional syringes and over syringes of the above composite type with respect to ensuring protection of the needle prior to use, and to putting the needle out of reach after use, making it impossible to reuse the needle.

It is known that the needle can be isolated by means of a tubular sheath that slides on the body of the syringe, which sheath is placed around the needle from a position in which it uncovers the needle. Mention may be made, for example, of syringes as described in the documents U.S. Pat. No. 4,911,693 and EP-A-0 250 104.

The device described in the first document is adapted to syringes having long needles, since the device is carried by the needle only. It is therefore unsuitable for cartridge syringes of the kind used in dentistry, in particular.

The device described in the second document does not provide a genuine guarantee of preventing syringe reuse, since the locking members are accessible to anyone seeking to manipulate them.

SUMMARY OF THE INVENTION

The invention seeks to remedy these drawbacks, and to this end it provides a protection device for the needle of an injection syringe, including, in known manner, a cylindrical body closed at one of its ends by a transverse wall in which the needle is implanted and fitted with a needle protector suitable for sliding along the body between two positions that are mutually separated in the axial direction, forming a moving protective sheath for the end of the needle, guiding and indexing elements being provided between the body and the protector to allow the needle to be uncovered and subsequently covered again by the sheath once only. According to one of the main characteristics of the invention, the indexing elements include a member secured to the protector that is situated in a zone thereof which is inaccessible from the outside, and that projects from its inside surface to bear resiliently against a guide surface of the other element, said surface being provided in its end portion adjacent to the needle with a recess for irreversibly receiving the locking member of the protector in its position where the needle is fully covered.

With a cartridge needle, the above disposition makes it possible to install a flask of substance to be injected in the needle carrier without uncovering the needle, and then to uncover the needle over a length that is sufficient to correspond to the depth it is to penetrate into tissue, and finally, after the injection has been performed, to cover the needle again so as to protect the person handling it and to make the syringe unusable.

In an embodiment of the invention, the protector has a tubular first portion which is of large diameter carrying the locking member and which is extended by a portion of small diameter forming the moving sheath for the end of the needle.

This member may be implemented in any practical manner: for example it may be an elastically deformable ring that is split radially and that, when received like a spring clip in a groove of the protector, is capable of sliding along the body so as to be moved into a circular groove thereof in which it contracts, the protector thus being held in its needle-uncovering position, and from which it can be extracted by pushing the protector towards the needle so as to be received irreversibly in another groove of the body that constitutes the above-mentioned recess, thus holding the protector in its needle-disabling position.

In another embodiment, the locking member is constituted by the free end of a resilient tongue projecting radially inside the large diameter portion of the protector, the guide surface being constituted by a groove formed in the body and having two parallel longitudinal branches interconnected by a circumferential portion at their ends furthest from the needle, one of the longitudinal branches of said groove including a recess at its opposite end for receiving the free end of the resilient tongue.

In a variant of this embodiment, the branch that does not include the recess includes a plurality of ratchets each constituting an abutment co-operating with the resilient tongue to cause it to be retracted in the needle-uncovering direction while preventing the protector from sliding in the needle-covering direction. This variant makes it possible to adjust the length of the needle to be uncovered as a function of the depth to which it is to penetrate into tissue during injection.

In a variant embodiment, the guide surface is formed on a slideway applied to the outside surface of the wall of the cylindrical body of the needle. This feature makes it possible to adapt the device of the invention to any of the syringes on the market, without it being necessary to manufacture the bodies of the syringes specially.

Other characteristics and advantages of the invention appear from the following description of embodiments.

BRIEF DESCRIPTION OF THE INVENTION

Reference is made to the accompanying drawing, in which:

FIG. 1 is a diagrammatic fragmentary axial section view through one embodiment of a device of the invention;

FIG. 2 shows a second embodiment of the device of the invention; and

FIG. 3 shows a variant of the FIG. 2 embodiment.

DESCRIPTION OF THE PREFERRED EMBODIMENTS

In the figures, an injector 1 is shown comprising, in conventional manner, two portions: the needle support 2 being designed to receive a flask 4 of substance to be injected, while the portion 3 is designed to enclose the support 2 and to provide the piston 5 for propelling the liquid by acting on a moving wall of the flask 4.

The support 2 constitutes a support for the injection needle 6 such that it perforates a perforatable wall of the flask and projects outwards from the support 2. This external portion of the needle is to be protected against the outside atmosphere (prior to use) and to be made inaccessible (after use) so as to protect people handling it and so as to make it impossible to reuse the needle.

According to the invention, this is done by the needle support 2 being fitted with a cylindrical slideway 7 which, in FIG. 1, is shown applied to the wall of the support 2 while in FIG. 2 it constitutes the wall itself.

The slideway 7 includes means for guiding and stopping translation motion of a needle protector 8 which is cylindrical in shape, having a large diameter portion 9 that co-operates slidably with the slideway 7, and a small diameter portion 10 that extends from the large diameter 9 longitudinally so as to cover the needle 6.

Over a length L, the large diameter portion 9 of the protector 8 has an inside diameter equal to the outside diameter of the cylindrical surface of the slideway 7, thus forming a bearing surface for providing mutual sliding guidance therebetween. This bearing surface has a groove 11 hollowed out therein which is inaccessible from the outside of the protector and in which a resilient split ring 12 is received whose unstressed diameter is less than the outside diameter of the slideway 7. The rear face 13 of the ring is chamfered. The end of the slideway opposite from the needle is provided with a groove 14 in which the ring 12 can contract to some extent when it comes in register therewith. The ring thus forms an axial indexing member for the protector on the slideway. The groove 14 also has a conical wall 15 which forms a sliding ramp for the chamfer of rear face 13 so as to enable the ring 12 to be extracted from the groove 14 when the protector moves towards the needle.

The slideway 7 includes a second groove 16 at its end closed to the needle. This groove has radial edges and is likewise capable of receiving a fraction of the ring 12 when the ring contracts into said groove. The ring 12 is then received in part only in said groove 16 but in irreversible manner, and axial locking between the protector and the slideway becomes final.

In FIG. 1, it may be observed that the groove 16 is occupied by a secondary ring 17 which is also resilient but which, unlike the ring 12, tends to expand diametrically against the inside wall of the protector 8. This inside wall has a secondary groove 18 formed therein that comes over the ring 17 when the ring 12 lies over the groove 14. At that moment, the ring 17 retracts fully into the groove 18 and then continues to move with the protector 8 as it moves to cover the needle again. The role of the ring 17 is firstly to make it easy to install the protector 8 on the slideway 7 when assembling the device by preventing the ring 12 from contracting into the groove 16, and secondly to constitute a stop abutment that prevents the protector from being disassembled from the slideway, with this being achieved by co-operating with a small inside shoulder 19 presented on the inside of the wall of the protector 8.

The slideway 7 may include more than one groove such as 16 so as to enable a plurality of different lengths of needle to be uncovered. In which case, the groove 18 is placed in such a manner as to receive the ring 17 when the ring 12 has reached the first groove in the slideway 7.

Finally, it will be observed that a spring 20 is present between the slideway 7 and the protector 8, being received in the protector, and urging the protector towards the needle. At least one disk 21 is disposed between the needle and the protector inside the protector so as to form an element that holds the needle against buckling while it is being inserted into the tissue of a patient. The disk has a cutout on its edge to pass the spring.

From the figure, it will be understood that the protector 8 can easily be pushed towards the needle support 2 in order to uncover a greater or lesser length of the needle 6 prior to injection and, after use, it can be returned or allowed to return automatically under drive from the spring to its initial position where it covers the needle in final manner. Since the locking means are inaccessible, easy reuse of the syringe is made impossible.

In the variant of FIG. 2, the guidance and indexing means between the protector and the slideway (which in this case is the body or needle support 2 itself of the syringe) are constituted on the slideway by a U-shaped groove 22 whose two branches 23 and 24 extend along two different generator lines of the slideway and are interconnected by a circumferential groove 25 that connects them together transversely, and on the protector by a resilient tongue 26 that projects inside the protector into the branch 23 of the groove 22. Within this branch, there is no hindrance to sliding in the needle-uncovering direction. Advantageously, particularly when a spring such as 20 is used, the end of the branch 23 is fitted with ratchets 27 that co-operate with the tongue 26 in a pawl-like manner so as to prevent the protector returning towards the needle, while leaving the tongue free to retract and pass over the ratchets during movement in the opposite direction. In the other branch, the bottom 28 slopes slightly upwards towards the needle and is subsequently terminated by a recess 29 from which the pawl cannot be extracted. Movement of the protector is then finally prevented. To achieve such prevention of movement, it is appropriate to push the protector 8 towards the circumferential portion 25 of the groove 22 and to rotate it to place the tongue 26 in the branch 24, thereby enabling the needle to be covered again under assistance from the spring.

FIG. 3 shows another variant of the embodiment in which the protector is made in two pieces: an inner piece 30 of strong material, e.g. polycarbonate, and including a locking pawl, and an outer piece 31 of material that is similar or different, and that is secured to the inner portion by gluing, welding, etc. . . . and that constitutes a sleeve carrying the smaller diameter portion and enclosing the inner piece, thus making the locking pawl inaccessible by covering it. The body of the syringe or the support 2, slideway 7 includes a U-shaped groove as described before, but in this case one of the branches originates in a circular groove 33 that constitutes the housing for the pawl in the protective position prior to use. The end of the other branch is provided with a recess 29 from which the pawl cannot be extracted. In order to avoid replacing the protector in its first position, the circumferential portion 34 interconnecting the two branches of the groove may co-operate with the end of the first branch to define a non-return ratchet 35 of the protector preventing it from returning towards its first position.

The invention is not limited to the description given above. It is equally applicable to various embodiments that are not shown such as those that use other guidance and indexing means for the protector on the slideway (insert or metal pawls . . . ). Similarly, the disposition of the pawl and of the slideway could be inverted relative to that described.

I claim:

1. A needle apparatus including a support body having a cylindrical wall and an end transverse wall in which a needle is implanted, a needle protector slidable along an external cylindrical surface of the support body between two positions, with respect to the support body which are axially distant each from the other, said protector forming a moving protective sheath for an end of the needle, guiding and indexing elements being provided between support body and the protector to allow the needle to be uncovered and subsequently covered again by the sheath once only, said indexing elements including a locking member secured to the protector and projecting inwardly to engage resiliently a groove formed on said external cylindrical surface of said support body and a recess for irreversibly receiving said locking member of the protector as the needle is fully covered by said protector, wherein said protector comprises an inner portion and an outer portion engaged one in the other, said inner portion being entirely housed in said outer portion and said locking member being constituted by a free end of a resilient tongue projecting radially inside the protector and carried by said inner portion while said outer portion forms a sleeve that prevents access to the inner portion, and wherein said groove has two parallel longitudinal branches interconnected by a circumferential portion at ends thereof furthest from said needle, one of the longitudinal branches of said groove including said recess at an end opposite to said circumferential portion for receiving the free end of said resilient tongue.

2. Apparatus according to claim 1 wherein said outer portion of the protector has two adjacent tubular sections, a first section being of a larger diameter carrying said inner portion and a second section being of a smaller diameter forming the moving sheath for the end of the needle.

3. Apparatus according to claim 2, wherein the resilient tongue is coupled between the protector and the support needle in the larger diameter portion of said protector, said tongue urging the protector into its position where it covers the needle in full.

4. Apparatus according to claim 2, wherein the larger diameter portion of the protector includes at least one element for holding the needle in a center of the protector.

5. Apparatus according to claim 1, wherein the branch of said groove that does not include the recess includes a plurality of ratchets each constituting an abutment cooperating with the resilient tongue to cause it to be retracted in a needle-uncovering direction while preventing the protector from sliding in a needle-covering direction.

6. Apparatus according to claim 1, wherein said groove is formed on a slideway disposed on the outside surface of the wall of the cylindrical support body of the needle.

* * * * *